(12) United States Patent
Gupta et al.

(10) Patent No.: US 7,504,494 B2
(45) Date of Patent: Mar. 17, 2009

(54) MULTIPLEX PCR ASSAY

(76) Inventors: Vishali Gupta, Postgraduate Institute of Medical Education & Research, Department of Immunopathology, Sector 12, Pgimer, Chandigarh (IN) 160 012; Naresh Sachdeva, 1550 NW. 10th Ave., Ste 118, Miami, FL (US) 33136; Amod Gupta, Postgraduate Institute of Medical Education & Research, Department of Immunopathology, Sector 12, Pgimer, Chandigarh (IN) 160 012; Sunil K. Arora, Postgraduate Institute of Medical Education & Research, Department of Immunopathology, Sector 12, Pgimer, Chandigarh (IN) 160 012; Pradeep Bambery, Postgraduate Institute of Medical Education & Research, Department of Immunopathology, Sector 12, Pgimer, Chandigarh (IN) 160 012

( * ) Notice: Subject to any disclaimer, the term of this patent is extended or adjusted under 35 U.S.C. 154(b) by 0 days.

(21) Appl. No.: 11/598,071

(22) Filed: Nov. 13, 2006

(65) Prior Publication Data

US 2007/0218474 A1   Sep. 20, 2007

(30) Foreign Application Priority Data

Nov. 14, 2005   (IN) .................... 3044/DEL/2005

(51) Int. Cl.
*C07H 21/04* (2006.01)
*C12P 19/34* (2006.01)
(52) U.S. Cl. .................. 536/24.32; 435/91.2
(58) Field of Classification Search ................ None
See application file for complete search history.

(56) References Cited

U.S. PATENT DOCUMENTS

| 2001/0014447 A1* | 8/2001 | Milhausen | 435/6 |
| 2004/0241654 A1* | 12/2004 | Das et al. | 435/6 |
| 2007/0190545 A1* | 8/2007 | Gupta et al. | 435/6 |
| 2007/0207453 A1* | 9/2007 | Gupta et al. | 435/5 |

FOREIGN PATENT DOCUMENTS

JP   06-339399   * 12/1994

OTHER PUBLICATIONS

Dabil et al., "Validation of a Diagnostic Multiplex Polymerase Chain Reaction Assay for Infectious Posterior Uveitis," Arch. Opthalmol., Sep. 2001, vol. 119, p. 1315-1322.*
Dolan et al., "Genetic content of wild-type human cytomegalovirus," J. Gen. Virol., May 2004, vol. 85, pp. 1301-1312.*
Buck et al., "Design Strategies and Performance of Custom DNA Sequencing Primers," Biotechniques, Sep. 1999, vol. 27, No. 3, pp. 528-536.*
Monforte et al, "A comparision of brain biopsy and CSF-PCR in the diagnosis of CNS lesions in AIDS patients," J. Neurol., 1997, vol. 244, pp. 35-39.*
Shimomoto et al., "Detection of Pneumocystis carinii, Mycobacterium tuberculosis, and Cytomegalovirus in Human Immunodeficiency Virus (HIV)-infected Patients with Hemophilia by Polymerase Chain Reaction of Induced Sputum Samples," Internal Med., 1995, vol. 34, No. 10, pp. 976-981.*
Armstrong et al, "Human Immunodeficiency Virus—Associated Fever of Unknown Origin: A Study of 70 Patients in the United States and Review," Clinc. Infect. Dis., 1999, vol. 28, pp. 341-345.*
Zhang et al., *"Multiplex Polymerase Chain Reaction for Detection of Herpes Simplex Virus Type 1, Type 2, Cytomegalovirus, and Varicella-Zoster Virus in Ocular Viral Infections"*; Jpn J. Ophthalmology, 47, pp. 260-264, 2003.
Markoulatos et al., *Laboratory Diagnosis of Common Herpesvirus Infections of the Central Nervous System by a Multiplex PCR Assay*, J. Clinical Microbiology, 39(12); pp. 4426-4432, 2001.
Lohmann et al., *"Improved Detection of Microorganisms by Polymerase Chain Reaction in Delayed Endophthalmitis after Cataract Surgery"*, Amer. Acad. Ophthalmology, pp. 1047-1051, 2000.

* cited by examiner

*Primary Examiner*—Kenneth R. Horlick
*Assistant Examiner*—Molly E Baughman
(74) *Attorney, Agent, or Firm*—Venable LLP; Catherine M. Voorhees; Nancy J. Axelrod

(57) ABSTRACT

This invention relates to a multiplex PCR assay capable of screening or detecting the relevant microbial organism specific to *Mycobacterium tuberculosis, Toxoplasma gondii*, pathogenically important fungii and cytomegalo virus (CMV) in a sample, comprising a reaction mixture of a combination of 4 sets of primers, one of said primer for detection of *Mycobacterium tuberculosis*, a second of said primer for detection of *Toxoplasma gondii*, a third primer for the detection of pathogenically important fungi and a fourth primer for the detection of CMV, said primers being compatible to each other.

5 Claims, No Drawings

```
SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccgctgcca gtcgtcttcc                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcctcgcga gtctaggcca                                                    20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggaactgcat ccgttcatga g                                                  21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctttaaagc gttcgtggtc                                                    20
```

```
<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
actttcgatg gtaggatag                                                   19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgatcgtctt cgatcccta                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtacacgcac gctggttacc                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtagaaagcc tcgacatcgc                                                  20
```

MULTIPLEX PCR ASSAY

FIELD OF INVENTION

This invention relates to multiplex PCR assay capable of identifying a particular microbial organism in a sample.

BACKGROUND OF THE INVENTION

Monoplex PCRs is a molecular technique for amplification of a selected gene fragment of the genome of any organism or cell using a specific set of primers specifically designed for that purpose. These primers can recognize and anneal (bind) to their pre-determined (complimentary) sequence on the genome of that cell/organism. Then the reagents including the enzyme, buffers and the nucleotide mix (building blocks) are mixed together in proportion and put at temperature and conditions so that the enzyme can put the building blocks (nucleotides) in pre-specified sequence as per the complementarities to template (parent) strand of DNA.

Such monoplex PCR for diagnosing infections like Cytomegalo virus (CMV), Herpes simplex virus (HSV), Vericella zoster virus (VZV), Human Immunodeficiency virus (HIV), *Toxoplasmosis gondii*, *Mycobacterium tuberculosis*, Lyme disease and diseases like lymphomas and Whipple disease have been established. Thus, Monoplex PCR for any infection is known in the art. However, one major impediment to this technique is that one needs to perform a separate PCR reaction for each pathogen that could be time consuming and prohibitively expensive especially if one needs to test for a large number of potential pathogens. Also the monoplex examination would tax the available sample volume that might be very small in situation like intraocular samples.

Multiplex PCR assay is capable of screening various microbial organisms simultaneously or identify different alleles of one organism. In a multiplex PCR, a different cocktail of reagents is used for carrying all other ingredients of a reaction mix as in monoplex PCR situation in addition to the specifically designed primers for all the organisms which are to be identified or detected. However, in Multiplex PCR, the primers and the conditions that are applicable in a monoplex setting no longer produce same results because the primers for different organisms interfere with each other and reduce the sensitivity as well as specificity of assay. Thus both primer selection as well as optimization of conditions and concentration of reagents used need to be standardized, keeping in view the 'nature' of each and every primer as well as requirement of the sensitivity in that particular situation.

Dabil and coworkers have published earlier a technique of multiplex PCR assay, by using novel set of primers for a panel of common pathogens including CMV, HSV, VZV and *Toxoplasma gondii* (Ref: Dabil H, Boley M L, Schmitz T M and Van Gender R N. Validation of a diagnostic multiplex polymerase chain reaction assay for infectious posterior uveitis. Archieves of Opthalmol 2001; 119:1315-22). Persson and Oslen have published Multiplex PCR reaction for identification of *Campylobacter Coli* and *Campylobacter jejuni* from pure cultures and directly on stool samples (Persson S and Oslen K E. J Med Microbiol. 2005; 54:1043-7).

OBJECTS OF THE INVENTION

An object of this invention is to propose a multiplex PCR assay capable of identifying the relevant microbial organism present in a sample. Another object of this invention is to propose primers for detection of *Mycobacterium tuberculosis*, *Toxoplasma gondii*, pathogenically important fungii and cytomegalo virus (CMV) present in a sample.

Further object of this invention is to propose a reaction mixture which can detect two or three organism in a sample at a time.

SUMMARY OF THE INVENTION

According to this invention there is provided a multiplex PCR assay capable of screening or detecting the relevant microbial organism specific to *Mycobacterium tuberculosis*, *Toxoplasma gondii*, pathogenically important fungii and cytomegalo virus (CMV) in a sample, comprising a reaction mixture of a combination of 4 sets of primers, one pair of said primers for detection of *Mycobacterium tuberculosis*, a second pair of said primers for detection of *Toxoplasma gondii*, a third primer pair for the detection of pathogenically important fungi and a fourth primer pair for detection of CMV, said primers being compatible to each other.

DETAILED DESCRIPTION OF THE INVENTION

The present invention relates to multiplex PCR reactions for a quadruplex for *Mycobacterium tuberculosis*, Pathogenically important Fungi, Toxoplasmosis and CMV.

Primer *Mycobacterium tuberculosis* having the following sequence:

```
MPB1: TCC GCT GCC AGT CGT CTT CC   (SEQ ID NO: 1)
MPB2: GTC CTC GCG AGT CTA GGC CA   (SEQ ID NO: 2)
```

For *Toxoplasma gondii*:

```
B1F: GGA ACT GCA TCC GTT CAT GAG   (SEQ ID NO: 3)
B1R: TCT TTA AAG CGT TCG TGG TC    (SEQ ID NO: 4)
```

For pathogenically important fungi:

```
B2F: ACT TTC GAT GGT AGG ATA G     (SEQ ID NO: 5)
B4R: TGA TCG TCT TCG ATC CCC TA    (SEQ ID NO: 6)
```

For Cytomegalo Virus (CMV):

```
ACMVF: GTA CAC GCA CGC TGG TTA CC  (SEQ ID NO: 7)
ACMVR: GTA GAA AGC CTC GAC ATC GC  (SEQ ID NO: 8)
```

Concentration of reagents was standardized in the quadruplex PCR reaction mix of 100 μl:

| (Concentration of minimal detectable DNA of the particular organism conforms to sensitivity of assay) | |
|---|---|
| Distilled water | 64.5 μl |
| 10X Assay Buffer | 10.0 μl |
| (10X buffer constituents: 0.1 M Tris-HCl, pH 8.8, 15 mM MgCl2, | |
| 25 mM MgCl$_2$ | 2.0 μl (effective: 2.0 mM) |
| 10 mM dNTPs | 2.5 μl (effective 250 μM) |
| 50 pmoles/μl pr-B1F | 1.25 μl (effective 0.625 pmoles/μl) |
| 50 pmoles/μl Pr-B1R | 1.25 μl (effective 0.625 pmoles/μl) |
| 50 pmoles/μl pr-B2F | 1.0 μl (effective 0.5 pmoles/μl) |
| 50 pmoles/μl pr-B4R | 1.0 μl (effective 0.5 pmoles/μl) |
| 50 pmoles/μl pr-MpB1 | 1.25 μl (effective 0.625 pmoles/μl) |
| 50 pmoles/μl pr-MpB2 | 1.25 μl (effective 0.625 pmoles/μl) |
| 50 pmoles/μl Pr-ACMVF | 1.25 μl (effective 0.625 pmoles/μl) |
| 50 pmoles/μl Pr-ACMVR | 1.25 μl (effective 0.625 pmoles/μl) |
| 5 μ/μl Taq DNA pol | 2.0 μl (effective 10 units) |
| Template DNA | 2.0 μl of each organism |

Thermo Cycling Conditions:

The thermocycling was carried out for 35 cylces, with denaturation at 94° C. for 45 sec, annealing at 56° C. for 45 sec and extension at 72° C. also for 45 sec with last cycle of extension of 7 mins.

We claims:

1. A multiplex PCR assay mixture for screening or detecting *Mycobacterium tuberculosis*, *Toxoplasma gondii*, pathogenically important fungi and cytomegalo virus (CMV) in a sample, comprising a combination of 4 sets of primers, one of said primer sets for the detection of *Mycobacterium tuberculosis*, a second of said primer sets for the detection of *Toxoplasma gondii*, a third primer set for the detection of pathogenically important fungi and a fourth primer set for the detection of CMV, said primers being compatible to each other, wherein the primer set for *Mycobacterium tuberculosis* is:

```
MPB1: TCC GCT GCC AGT CGT CTT CC       (SEQ ID NO:1)

MPB2: GTC CTC GCG AGT CTA GGC CA       (SEQ ID NO:2)
``` for *Toxoplasma gondii* is:

```
B1F: GGA ACT GCA TCC GTT CAT GAG      (SEQ ID NO:3)
B1R: TCT TTA AAG CGT TCG TGG TC       (SEQ ID NO:4)
``` for pathogenically important fungi is:

```
B2F: ACT TTC GAT GGT AGG ATA G        (SEQ ID NO:5)
B4R: TGA TCG TCT TCG ATC CCC TA       (SEQ ID NO:6)
``` for Cytomegalo Virus (CMV) is:

```
ACMVF: GTA CAC GCA CGC TGG TTA CC     (SEQ ID NO:7)
ACMVR: GTA GAA AGC CTC GAC ATC GC.    (SEQ ID NO:8)
```

2. The multiplex PCR assay mixture as claimed in claim 1 wherein said PCR assay mixture comprises, by volume percent:

| |
|---|
| 10% of a 10X Assay Buffer comprising 0.1 M Tris-HCL, PH 8.8, |
| 15 mM MgCl₂, |
| 2.0% of 25 mM MgCl₂ |
| 2.5% of 10 mM dNTPs |
| 1.25% of 50 pmoles/µl pr-B1F |
| 1.25% of 50 pmoles/µl Pr-B1R |
| 1.0% of 50 pmoles/µl pr-B2F |
| 1.0% of 50 pmoles/µl pr-B4R |
| 1.25% of 50 pmoles/µl pr-MpB1 |
| 1.25% of 50 pmoles/µl pr-MpB2 |
| 1.25% of 50 pmoles/µl Pr-ACMVF |
| 1.25% of 50 pmoles/µl Pr-ACMVR |
| 2.0% of 5 u/µl Taq DNA pol |
| 2.0% of Template DNA of each organism. |

3. A method for identifying or detecting *Mycobacterium tuberculosis, Toxoplasma gondii*, pathogenically important fungi and cytomegalo virus (CMV) in a sample comprising the steps of:

preparing a mixture of primers sets compatible to each other, in a multiplex PCR assay mixture;

treating the sample with the primers and carrying out thermo cycling for 35 cycles with denaturation, annealing at 54° C. for 45 sec and extension at 72° C. for 45 sec, with a last cycle of extension of 7 mins, thereby identifying or detecting the micro-organisms, wherein the primer set For *Mycobacterium tuberculosis* is:

```
MPB1: TCC GCT GCC AGT CGT CTT CC    (SEQ ID NO:1)

MPB2: GTC CTC GCG AGT CTA GGC CA    (SEQ ID NO:2)
```

For *Toxoplasma gondii* is:

```
B1F: GGA ACT GCA TCC GTT CAT GAG    (SEQ ID NO:3)

B1R: TCT TTA AAG CGT TCG TGG TC     (SEQ ID NO:4)
```

For pathogenically important fungi is:

```
B2F: ACT TTC GAT GGT AGG ATA G      (SEQ ID NO:5)

B4R: TGA TCG TCT TCG ATC CCC TA     (SEQ ID NO:6)
```

For Cytomegalo Virus (CMV) is:

```
ACMVF: GTA CAC GCA CGC TGG TTA CC   (SEQ ID NO:7)

ACMVR: GTA GAA AGC CTC GAG ATC GC.  (SEQ ID NO:8)
```

4. The method as claimed in claim 3 wherein said reaction mixture comprises, by volume percent:

| |
|---|
| 10% of a 10X Assay Buffer comprising 0.1 M Tris-HCL, PH 8.8, |
| 15 mM MgCl₂, |
| 2.0% of 25 mM MgCl₂ |
| 2.5% of 10 mM dNTPs |
| 1.25% of 50 pmoles/µl pr-B1F |
| 1.25% of 50 pmoles/µl Pr-B1R |
| 1.0% of 50 pmoles/µl pr-B2F |
| 1.0% of 50 pmoles/µl pr-B4R |
| 1.25% of 50 pmoles/µl pr-MpB1 |
| 1.25% of 50 pmoles/µl pr-MpB2 |
| 1.25% of 50 pmoles/µl Pr-ACMVF |
| 1.25% of 50 pmoles/µl Pr-ACMVR |
| 2.0% of 5 u/µl Taq DNA pol |
| 2.0% of Template DNA of each organism. |

5. A method as claimed in claim 3 wherein said themocycling with denaturation is carried out at 94° C. for 45 seconds.

* * * * *